United States Patent
Koblish

(10) Patent No.: US 6,711,444 B2
(45) Date of Patent: Mar. 23, 2004

(54) METHODS OF DEPLOYING HELICAL DIAGNOSTIC AND THERAPEUTIC ELEMENT SUPPORTING STRUCTURES WITHIN THE BODY

(75) Inventor: Josef V. Koblish, Palo Alto, CA (US)

(73) Assignee: Scimed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/929,936

(22) Filed: Aug. 15, 2001

(65) Prior Publication Data

US 2002/0004644 A1 Jan. 10, 2002

Related U.S. Application Data

(63) Continuation-in-part of application No. 09/832,612, filed on Apr. 10, 2001, which is a continuation-in-part of application No. 09/447,186, filed on Nov. 22, 1999, now Pat. No. 6,542,781.

(51) Int. Cl.[7] .............................. A61B 5/04; A61N 1/05
(52) U.S. Cl. ...................................... 607/122; 600/373
(58) Field of Search ..................... 604/20–21, 104–109; 607/115, 119–123, 126–128; 300/372–374; 606/198

(56) References Cited

U.S. PATENT DOCUMENTS

| 4,419,094 A | 12/1983 | Patel |
|---|---|---|
| 4,650,466 A | 3/1987 | Luther |
| 4,706,671 A | 11/1987 | Weinrib |
| 4,834,724 A | 5/1989 | Geiss |
| 4,921,484 A | 5/1990 | Hillstead |
| 5,016,808 A | 5/1991 | Heil, Jr. |
| 5,054,501 A | 10/1991 | Chuttani |

(List continued on next page.)

FOREIGN PATENT DOCUMENTS

| EP | 0868922 A2 | 10/1998 |
|---|---|---|
| EP | 1042990 A1 | 10/2000 |
| WO | wo98/26724 | 6/1998 |
| WO | wo99/02096 | 1/1999 |
| WO | wo99/18878 | 4/1999 |
| WO | wo99/34741 | 7/1999 |
| WO | wo00/01313 | 1/2000 |
| WO | WO 01/37723 A2 | 5/2001 |

OTHER PUBLICATIONS

US Pat. Pub. No. 2001/0020174A1, filed Sep. 6, 2001.

*Primary Examiner*—Sharon Kennedy
(74) *Attorney, Agent, or Firm*—Henricks, Slavin & Holmes LLP

(57) ABSTRACT

A method of deploying a helical structure having at least one operative element within a bodily structure defining an orifice includes the steps of inserting at least a portion of the helical structure through the orifice in an uncoiled state and returning the helical structure to a coiled state while at least a portion of the helical structure is within the bodily structure such that the coiled helical structure engages the orifice.

17 Claims, 4 Drawing Sheets

U.S. PATENT DOCUMENTS

| | | |
|---|---|---|
| 5,163,431 A | 11/1992 | Griep |
| 5,228,442 A | 7/1993 | Imran |
| 5,239,999 A | 8/1993 | Imran |
| 5,279,299 A | 1/1994 | Imran |
| 5,411,546 A | 5/1995 | Bowald |
| 5,456,667 A | 10/1995 | Ham |
| 5,545,200 A | 8/1996 | West |
| 5,549,661 A | 8/1996 | Kordis |
| 5,582,609 A | 12/1996 | Swanson |
| 5,716,410 A | 2/1998 | Wang |
| 5,722,401 A | 3/1998 | Pietroski |
| 5,755,760 A | 5/1998 | Maguire |
| 5,814,028 A | 9/1998 | Swartz |
| 5,836,925 A | 11/1998 | Soltesz |
| 5,836,947 A | 11/1998 | Fleischman |
| 5,860,974 A | 1/1999 | Abele |
| 5,879,295 A | 3/1999 | Li |
| 5,891,112 A | 4/1999 | Samson |
| 5,938,660 A | 8/1999 | Swartz |
| 5,938,694 A | 8/1999 | Jaraczewski |
| 5,971,983 A | 10/1999 | Lesh |
| 5,972,019 A | 10/1999 | Engelson |
| 6,012,457 A | 1/2000 | Lesh |
| 6,016,809 A | 1/2000 | Mulier |
| 6,024,740 A | 2/2000 | Lesh |
| 6,064,902 A | 5/2000 | Haissaguerre |
| 6,071,274 A | 6/2000 | Thompson |
| 6,071,279 A | 6/2000 | Whayne |
| 6,071,281 A | 6/2000 | Burnside |
| 6,106,522 A | 8/2000 | Fleischman |
| 6,117,101 A | 9/2000 | Diederich |
| 6,152,920 A | 11/2000 | Thompson |
| 6,203,525 B1 | 3/2001 | Whayne |
| 6,233,491 B1 | 5/2001 | Kordis |
| 6,280,441 B1 | 8/2001 | Ryan |
| 6,325,797 B1 | 12/2001 | Stewart |
| 6,371,928 B1 | 4/2002 | Mcfann |
| 6,391,018 B1 | 5/2002 | Tanaka |
| 6,468,272 B1 | 10/2002 | Koblish et al. |
| 6,542,781 B1 | 4/2003 | Koblish et al. |
| 2001/0007070 A1 | 7/2001 | Stewart |

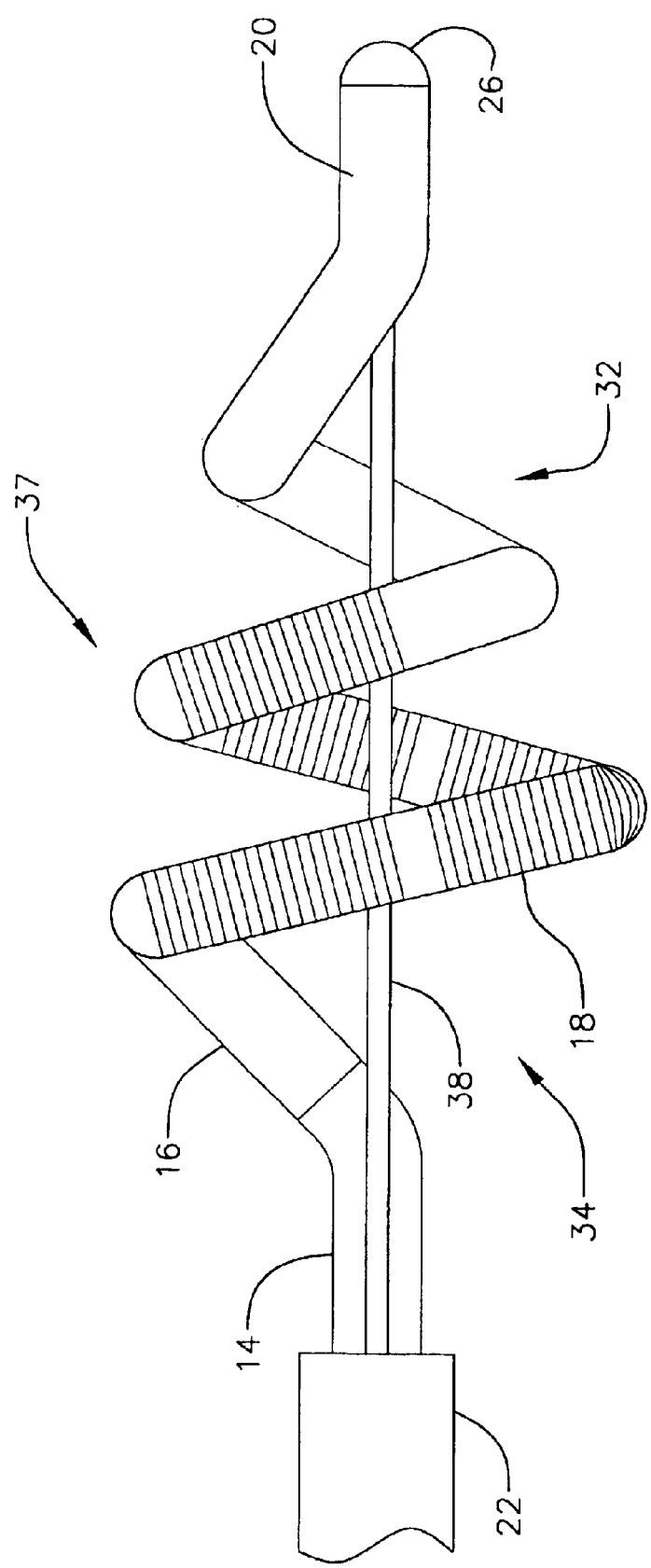

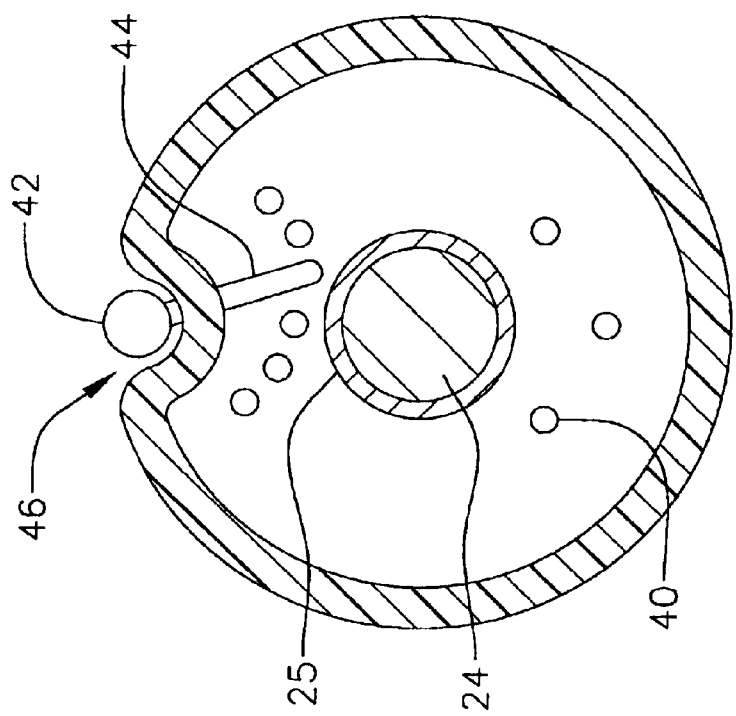
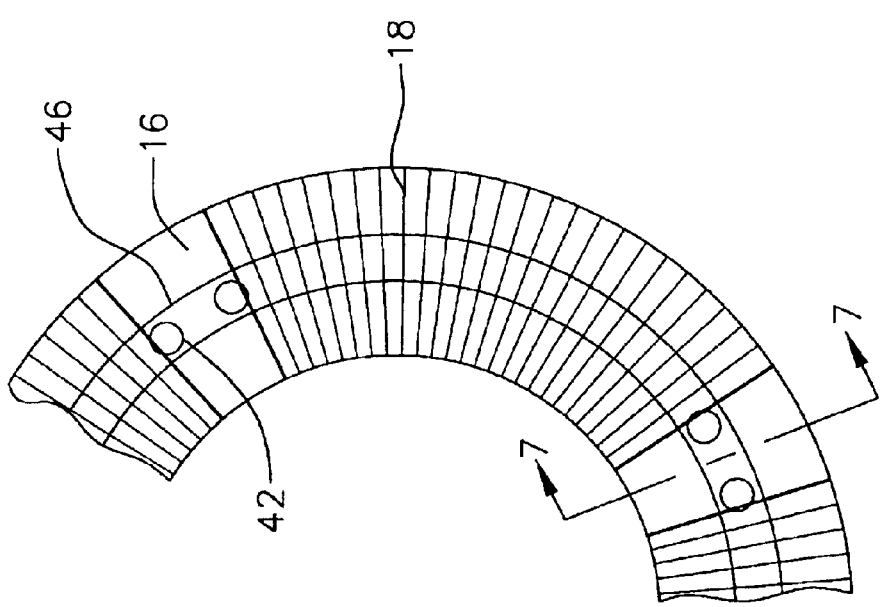

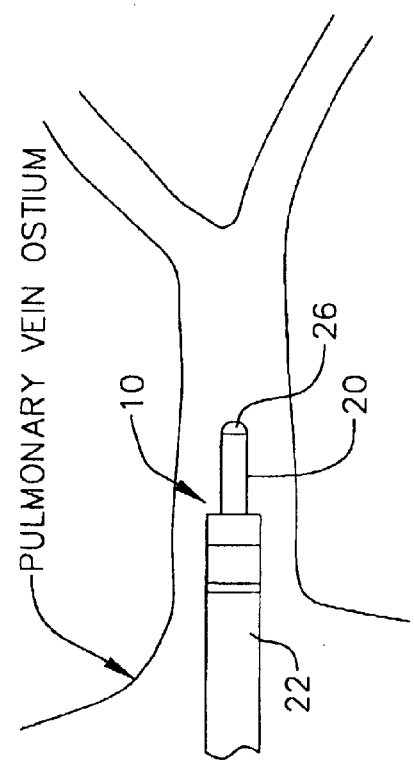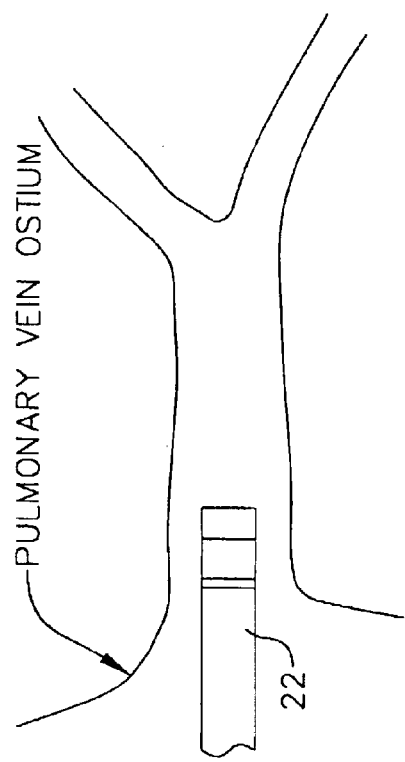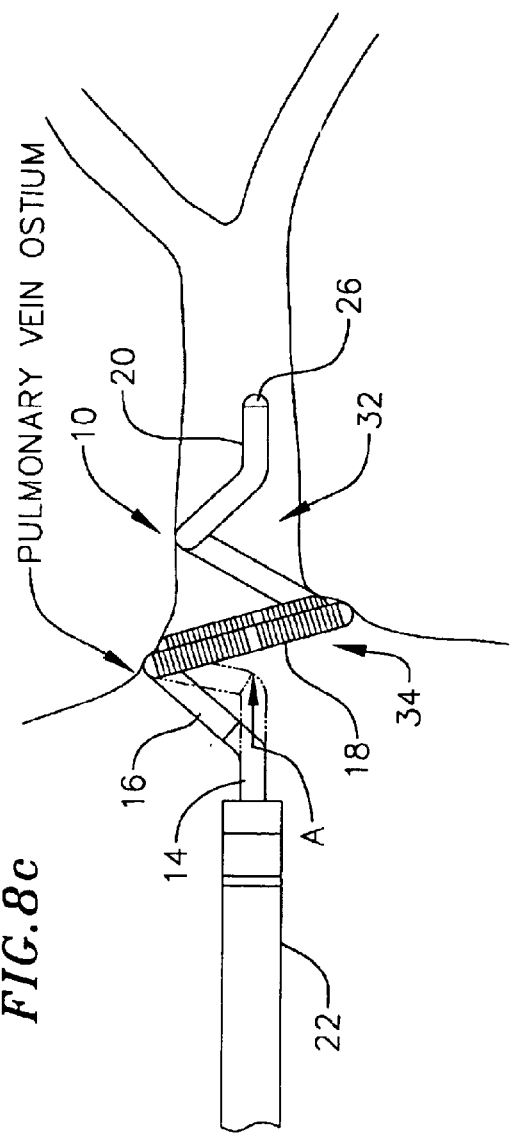

METHODS OF DEPLOYING HELICAL DIAGNOSTIC AND THERAPEUTIC ELEMENT SUPPORTING STRUCTURES WITHIN THE BODY

CROSS-REFERENCE TO RELATED APPLICATIONS

This application is a continuation-in-part of U.S. application Ser. No. 09/832,612, filed Apr. 10, 2001, and a continuation-in-part of U.S. application Ser. No. 09/447,186, filed Nov. 22, 1999, now U.S. Pat. No. 6,542,781, issued Apr. 1, 2003, each of which is incorporated herein by reference.

BACKGROUND OF THE INVENTIONS

1. Field of Inventions

The present inventions relate generally to medical devices that support one or more diagnostic or therapeutic elements in contact with body tissue and, more particularly, to methods of deploying helical devices that support one or more diagnostic or therapeutic elements.

2. Description of the Related Art

There are many instances where diagnostic and therapeutic elements must be inserted into the body. One instance involves the treatment of cardiac conditions such as atrial fibrillation and atrial flutter which lead to an unpleasant, irregular heart beat, called arrhythmia.

Normal sinus rhythm of the heart begins with the sinoatrial node (or "SA node") generating an electrical impulse. The impulse usually propagates uniformly across the right and left atria and the atrial septum to the atrioventricular node (or "AV node"). This propagation causes the atria to contract in an organized way to transport blood from the atria to the ventricles, and to provide timed stimulation of the ventricles. The AV node regulates the propagation delay to the atrioventricular bundle (or "HIS" bundle). This coordination of the electrical activity of the heart causes atrial systole during ventricular diastole. This, in turn, improves the mechanical function of the heart. Atrial fibrillation occurs when anatomical obstacles in the heart disrupt the normally uniform propagation of electrical impulses in the atria. These anatomical obstacles (called "conduction blocks") can cause the electrical impulse to degenerate into several circular wavelets that circulate about the obstacles. These wavelets, called "reentry circuits," disrupt the normally uniform activation of the left and right atria.

Because of a loss of atrioventricular synchrony, the people who suffer from atrial fibrillation and flutter also suffer the consequences of impaired hemodynamics and loss of cardiac efficiency. They are also at greater risk of stroke and other thromboembolic complications because of loss of effective contraction and atrial stasis.

One surgical method of treating atrial fibrillation by interrupting pathways for reentry circuits is the so-called "maze procedure" which relies on a prescribed pattern of incisions to anatomically create a convoluted path, or maze, for electrical propagation within the left and right atria. The incisions direct the electrical impulse from the SA node along a specified route through all regions of both atria, causing uniform contraction required for normal atrial transport function. The incisions finally direct the impulse to the AV node to activate the ventricles, restoring normal atrioventricular synchrony. The incisions are also carefully placed to interrupt the conduction routes of the most common reentry circuits. The maze procedure has been found very effective in curing atrial fibrillation. However, the maze procedure is technically difficult to do. It also requires open heart surgery and is very expensive.

Maze-like procedures have also been developed utilizing catheters which can form lesions on the endocardium (the lesions being 1 to 15 cm in length and of varying shape) to effectively create a maze for electrical conduction in a predetermined path. The formation of these lesions by soft tissue coagulation (also referred to as "ablation") can provide the same therapeutic benefits that the complex incision patterns that the surgical maze procedure presently provides, but without invasive, open heart surgery.

Catheters used to create lesions typically include a relatively long and relatively flexible body portion that has a soft tissue coagulation electrode on its distal end and/or a series of spaced tissue coagulation electrodes near the distal end. The portion of the catheter body portion that is inserted into the patient is typically from 23 to 55 inches in length and there may be another 8 to 15 inches, including a handle, outside the patient. The length and flexibility of the catheter body allow the catheter to be inserted into a main vein or artery (typically the femoral artery), directed into the interior of the heart, and then manipulated such that the coagulation electrode contacts the tissue that is to be ablated. Fluoroscopic imaging is used to provide the physician with a visual indication of the location of the catheter.

In some instances, the proximal end of the catheter body is connected to a handle that includes steering controls. Exemplary catheters of this type are disclosed in U.S. Pat. No. 5,582,609. In other instances, the catheter body is inserted into the patient through a sheath and the distal portion of the catheter is bent into loop that extends outwardly from the sheath. This may be accomplished by pivotably securing the distal end of the catheter to the distal end of the sheath, as is illustrated in U.S. Pat. No. 6,071,279. The loop is formed as the catheter is pushed in the distal direction. The loop may also be formed by securing a pull wire to the distal end of the catheter that extends back through the sheath, as is illustrated in U.S. Pat. No. 6,048,329. One lesion that proved difficult to form with conventional steerable and loop devices was the circumferential lesion that is formed within the pulmonary vein, or in the tissue surrounding the pulmonary vein, which isolates the pulmonary vein and cures ectopic atrial fibrillation.

More recently, helical structures have been developed that can be used to create circumferential lesions within or around bodily orifices and, in the context of the treatment of atrial fibrillation, within or around the pulmonary vein. Various examples of such helical structures are disclosed in U.S. application Ser. No. 09/832,612, which is entitled "Helical And Pre-Oriented Loop Structures For Supporting Diagnostic And Therapeutic Elements In Contact With Body Tissue." These structures are particularly advantageous because they may be used to create lesions within or around the pulmonary vein without occluding blood flow.

Heretofore, helical structures have been deployed within a patient by inserting them through a sheath in a collapsed state to a region that is adjacent to, and preferably aligned with, the target bodily orifice. The collapsed structure was then urged distally out of the sheath (or the sheath was retracted), thereby allowing the collapsed structure to assume its helical shape. Next, the helical structure was urged distally into contact with the tissue surrounding the orifice. With respect to the pulmonary veins, the helical structure was deployed within the left atrium and then urged distally into contact with the tissue associated with the pulmonary vein ostium.

The inventor herein has determined that, while useful, the conventional method of deploying a helical structure within a patient is susceptible to improvement.

SUMMARY OF THE INVENTION

A method of deploying a helical structure having at least one operative element within a bodily structure defining an orifice in accordance with one embodiment of a present invention includes the steps of inserting at least a portion of the helical structure through the orifice in an uncoiled state and returning the helical structure to a coiled state while at least a portion of the helical structure is within the bodily structure such that the coiled helical structure engages the orifice. Such a method typically results in superior tissue-operative element contact at the orifice than does coiling the helical structure in spaced relation to the orifice and then advancing the helical structure distally into contact with the orifice.

The deployment method is particularly useful in the treatment of a pulmonary vein with a tapered helical structure having one or more operative elements on the proximal coils. Here, the helical structure may be inserted into the pulmonary vein ostium prior to being returned to its coiled state. The tapered helical structure will deploy into the funnel-shaped ostium of the pulmonary vein in such a manner that the atrial tissue will distend and wrap around the helical structure as it wedges itself into position. So positioned, the operative element(s) will be forced against the pulmonary vein ostium and, as a result, tissue coagulation will only occur at the ostium and the likelihood of thermally activated in-vein stenosis will be reduced.

The above described and many other features and attendant advantages of the present inventions will become apparent as the inventions become better understood by reference to the following detailed description when considered in conjunction with the accompanying drawings.

BRIEF DESCRIPTION OF THE DRAWINGS

Detailed description of preferred embodiments of the inventions will be made with reference to the accompanying drawings.

FIG. 5 is a side view of another exemplary probe that may be used in conjunction with a present invention.

FIG. 6 is a partial end view of the probe illustrated in FIG. 1.

FIG. 7 is a section view taken along line 7—7 in FIG. 6.

FIGS. 8a–8c are side views showing various aspects of a deployment method in accordance with a preferred embodiment of a present invention.

DETAILED DESCRIPTION OF THE PREFERRED EMBODIMENTS

The following is a detailed description of the best presently known modes of carrying out the inventions. This description is not to be taken in a limiting sense, but is made merely for the purpose of illustrating the general principles of the inventions.

The detailed description of the preferred embodiments is organized as follows:

I. Introduction
II. Exemplary Helical Structures
III. Deployment of Helical Structures The section titles and overall organization of the present detailed description are for the purpose of convenience only and are not intended to limit the present inventions.

I. Introduction

The present inventions may be performed within body lumens, chambers or cavities for diagnostic or therapeutic purposes in those instances where access to interior bodily regions is obtained through, for example, the vascular system or alimentary canal and without complex invasive surgical procedures. For example, the inventions herein have application in the diagnosis and treatment of arrhythmia conditions within the heart. The inventions herein also have application in the diagnosis or treatment of ailments of the gastrointestinal tract, prostrate, brain, gall bladder, uterus, and other regions of the body. With regard to the treatment of conditions within the heart, the present inventions are designed to produce intimate tissue contact between a diagnostic or therapeutic device and target substrates within or around the pulmonary vein to, for example, treat ectopic atrial fibrillation.

The inventions may also be performed with probes other than catheter-based probes such as, for example, hand held surgical devices (or "surgical probes") which incorporate the disclosed helical structures. The distal end of a surgical probe may be placed directly in contact with the targeted tissue area by a physician during a surgical procedure, such as open heart surgery. Here, access may be obtained by way of a thoracotomy, median sternotomy, or thoracostomy. Exemplary surgical probes on which such helical structures may be mounted are disclosed in U.S. Pat. No. 6,142,994, which is incorporated herein by reference.

II. Exemplary Helical Structures

The present methods may be performed with a wide variety of helical structures, some of which are described below. Other exemplary helical structures are disclosed in aforementioned U.S. application Ser. No. 09/832,612. The present methods are not, however, limited to use with any particular helical structure.

Figure 2:
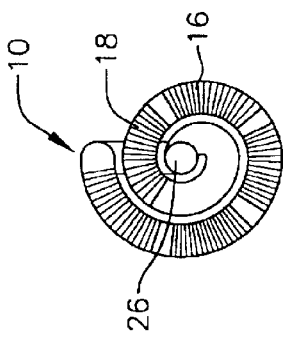
FIG. 2 is an end view of the probe illustrated in FIG. 1.
Figure 1:
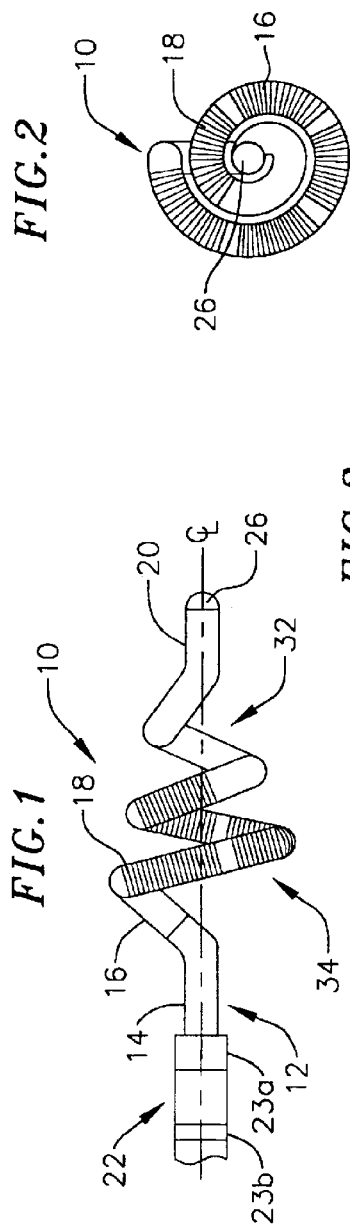
FIG. 1 is a side view of an exemplary probe that may be used in conjunction with a present invention.
Figure 3:
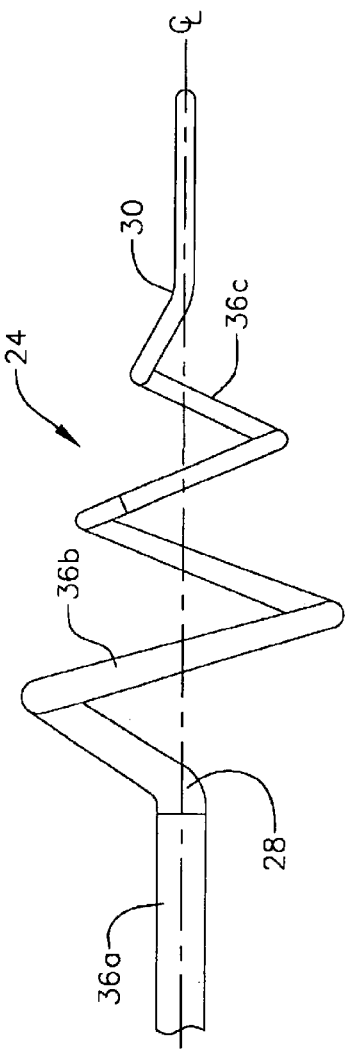
FIG. 3 is a side view of an exemplary core wire.
Figure 4:
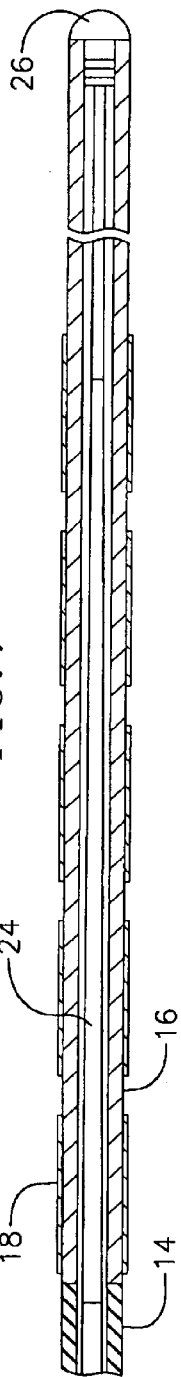
FIG. 4 is a section view of the distal portion of the probe illustrated in FIG. 1 in a straightened orientation.

As illustrated FIGS. 1–4, an exemplary catheter 10 includes a hollow, flexible catheter body 12 that is formed from two tubular parts, or members. The proximal member 14 is relatively long and is attached to a conventional catheter handle (not shown), while the distal member 16, which is relatively short, carries a plurality of spaced electrodes 18 or other operative elements. The proximal member 14 is typically formed from a biocompatible thermoplastic material, such as a Pebax® material (polyether block emide) and stainless steel braid composite, which has good torque transmission properties. The distal member 16 is typically formed from a softer, more flexible biocompatible thermoplastic material such as unbraided Pebax® material, polyethylene, or polyurethane. The proximal and distal members, which are about 5 French to about 9 French in diameter, are preferably either bonded together with an overlapping thermal bond or adhesively bonded together end to end over a sleeve in what is referred to as a "butt bond."

At least a portion of the distal member 16 has a generally helical shape that defines a longitudinal axis coincident with the longitudinal axis of the remainder of the catheter body 12. The number of revolutions (or "coils"), length, diameter, orientation and shape of the helical portion will vary from application to application. The helical portion of the distal member 16 in the embodiment illustrated in FIGS. 1–4, which may be used to create lesions in or around the pulmonary vein, revolves around the longitudinal axis of the catheter 10 two and one-half times. The helical portion also has a generally frusto-conical shape where the diameter decreases in the distal direction. The diameter may, alternatively, be substantially constant over the length of the helical portion. The helical portion defines an open area interior to the electrodes 18 through which blood or other bodily fluids can flow. As a result, the helical portion can be used to create a circumferential lesion in or around the pulmonary vein, or other bodily orifice, without occluding fluid flow.

An embodiment configured for use with the pulmonary veins will preferably have a proximal coil outer diameter that will cause the proximal portion to abut the pulmonary vein ostium (i.e. between about 15 mm and about 35 mm) and a distal coil outer diameter suitable for placement within the pulmonary vein (i.e. between about 5 mm and about 10 mm). The helical catheter 10 will, therefore, be self-centering when inserted into the pulmonary vein because the tapered helical portion will wedge itself against the pulmonary vein ostium and the internal wall of pulmonary vein itself, as described in greater detail below. Not only does this result in proper positioning of the electrodes 18, the wedging effect also prevents beating related movement of the heart from knocking the helical catheter 10 out of position once it is in place.

An anchor member 20 allows the catheter to be precisely located relative to the pulmonary vein (or other orifice), during certain methods of use. For example, the anchor member 20 is useful in those instances where the helical portion is deployed, either purposely or accidentally, within the left atrium and then advanced into contact with the pulmonary vein. In those instances where the helical portion is deployed within the pulmonary vein, the anchor member 20 will stabilizes the catheter during deployment and prevent undesirably movement of the helical portion at it exits the sheath 22 (described below). The anchor member 20 also helps maintain position after the helical portion has been deployed. The exemplary anchor member 20 is approximately 1 to 2 inches in length. Other lengths may be used, or the anchor member 20 may be eliminated altogether, to suit particular applications.

The exemplary catheter 10 illustrated in FIGS. 1–4 is not a steerable catheter and, accordingly, may be advanced though a conventional guide sheath 22 to the target location. The sheath 22, which should be lubricious to reduce friction during movement of the catheter 10, may be advanced into position over a guidewire or steerable catheter in conventional fashion. Alternatively, a steerable sheath may be provided. With respect to materials, the proximal portion of the sheath 22 is preferably a Pebax® and stainless steel braid composite and the distal portion is a more flexible material, such as unbraided Pebax®, for steering purposes. The sheath 22 should also be stiffer than the catheter body 12 and may be provided with a soft tip 23a, to prevent tissue damage, and/or a radiopaque tip marker 23b, to facilitate proper positioning of the distal end of the sheath within the patient. A sheath introducer, such as those used in combination with basket catheters, may be used when introducing the distal member 16 into the sheath 22.

The helical shape of the exemplary distal member 16 may be achieved through the use of a center support 24 (FIGS. 3 and 4) that is positioned inside the catheter body 12. The center support 24 is preferably formed from resilient inert wire, such as Nickel Titanium (commercially available under the trade name Nitinol®) or 17-7 stainless steel wire, with a portion thereof heat set into the desired helical configuration. The helical portion of the distal member 16 and center support 24 should be flexible enough that the helical portion will deflect and straighten out when pushed or pulled into the sheath, yet resilient enough that it will return to its helical shape when removed from the sheath. The proximal end of the center support 24 is secured to the handle, while the distal end is secured to a tip member 26, which is in turn secured to the distal end of the distal member 16 with adhesive. The center support 24 is also preferably housed in an insulative tube 25 (FIG. 7) formed from material such as Teflon™ or polyester.

The proximal and distal ends of the helical portion should be oriented at an angle relative to the longitudinal axis of the catheter 10 (preferably between about 30 and about 60 degrees and most preferably about 45 degrees) that facilitates a smooth transition as the distal member 16 is pushed or pulled into the sheath 22. To that end, the exemplary internal center support 24 includes pre-bent curved portions 28 and 30 (FIG. 3) that produce corresponding curves in the catheter body. The pre-bent curved portion 28 will typically be bent out of its pre-bent orientation when the catheter body 12 and helical portion are urged against tissue. The internal center support 24 will then generate a spring force that also urges the helical portion against the tissue and improves tissue/electrode contact. Additionally, because the curved portion 28 is located along the axis of the helical structure, the spring force will be distributed evenly around the circumference of the helical portion.

The center support may, alternatively, be formed from material such as actuator-type Nitinol® which has shape memory properties that are activated at a temperature higher than body temperature. The shape memory properties allow the physician to, for example, cause the helical portion of the distal member 16 to recoil from the state illustrated in FIG. 4 to the coiled state illustrated in FIG. 1 by energizing the electrodes 18. The amount of heat generated by the electrodes 18 during the recoiling should, however, be less than that required to coagulate tissue and form a lesion.

The helical portion of the exemplary catheter 10 illustrated in FIGS. 1–4 is also configured such that the distal region 32 is relatively flexible and the proximal region 34 is relatively stiff. As a result, there is a non-linear force distribution through the coils. The differences in stiffness allows the exemplary catheter to accomplish a number of normally competing goals. In those instances where the helical portion is either purposely or accidentally expanded within the left atrium, such that it must then be advanced into contact with a pulmonary vein after it recoils, the physician must often poke around within the atrium as attempts are made to insert the helical structure into the pulmonary vein. The more flexible distal region 32 will, of course, be less likely to traumatize tissue during this process. It is also important that the helical portion be predisposed to easily uncoil for placement within the sheath 22, remain uncoiled and slide though the sheath until it exits through the distal end of the sheath and re-coils, and then easily uncoil again when pulled back into the sheath after the procedure is completed. The stiffer the coils are, the more likely they are to resist uncoiling, which makes it more difficult to get the helical structure into the sheath, and to recoil within the sheath, which creates friction and makes it more difficult to slide the helical structure through the sheath. Thus, the more flexible distal region 32 will also improve these aspects of the procedure. Good tissue/electrode contact is another important goal in any lesion creation procedure. The stiffer proximal region 34 causes the electrodes 18 to press against the tissue with more force when lesions are being created.

Increasing the flexibility of the distal region 32 may be accomplished in a variety of ways. As illustrated for example in FIG. 3, the exemplary core wire 24 has three sections—a full cross-sectional area section 36a, a tapered section 36b and a reduced cross-sectional area section 36c. [Cross-sectional area is measured in a plane that is perpendicular to the centerline CL.] Although other shapes and sizes may be employed, the core wire 24 is preferably cylindrical in shape and has the following dimensions: the diameter of section 36a is about 0.022 inch, the diameter of section 36c is about 0.012 inch and, when in the straightened (or "uncoiled") state illustrated in FIG. 4, section 36b is about 4.25 inches in length and section 36c is about 3.00 inches in length. When in the coiled state illustrated in FIG. 3, the coiled region including section 36b and a portion of section 36c is about 1.25 inches in length and the remaining linear portion of section 36c (which is within the anchor member 34) is about 0.75 inch in length. Such a core wire will necessarily result in a distal region 32 that is less stiff than it would have been if the entire core wire had the diameter of section 36a. In order to insure that the distal region 32 is in fact less stiff than the proximal region 34, section 36c may be reduced in diameter and/or increased in length thereby causing section 36b to taper down to a smaller diameter and/or have a shorter length.

Other methods of increasing the flexibility of the distal region 32 include forming the distal member 16 from variable stiffness tubing. For example, the tubing may have two portions, i.e. a higher durometer proximal portion and a lower durometer distal portion secured to one another, or may be unitary and simply vary in stiffness continuously over its length from a higher durometer at the proximal end to a lower durometer at the distal end. The tubing used to form the distal member 16 may also be tapered such that the diameter of the tubing decreases from a larger diameter at the proximal end to a smaller diameter at the distal end. Here too, this may be accomplished by employing a two portion design, i.e. two portions having different, but constant diameters secured to one another, or a unitary design where the diameter drops continuously over the length of the tubing.

Referring to the exemplary catheter 37 illustrated in FIG. 5, a stylet 38 may be provided in order to increase the manipulability of the helical portion, especially in those instances where it is desirable to provide a core wire that has relatively low resiliency. The physician can manipulate the distal member 16 by moving stylet 38 distally and proximally, to stretch and contract the helical portion, or by rotating it in one direction or the other, to wind and unwind the helical portion and vary diameter. Prior to advancing the catheter 10 into the sheath 22, the stylet 38 will be moved to and held in its distal most position in order to straighten out the helical portion of the distal member 16. The stylet 38 will remain in this position until the helical portion of the distal member 16 is advanced beyond the distal end of the sheath 22.

The distal end of the stylet 38 enters the anchor member 20 through a small opening (not shown) in the catheter body 10 and is secured therein. The proximal end of the stylet 38 should be connected to a handle that allows the physician to move the stylet 24 proximally and distally relative to the catheter body 12 and also allows the physician to rotate the stylet relative to the catheter body. Examples of such handles are disclosed in aforementioned U.S. application Ser. No. 09/832,612. The stylet 38 should also be stiffer than the center support 24 and is preferably formed from inert wire such as Nitinol® or 17-7 stainless steel wire.

As noted above, the exemplary catheter 10 carries a plurality of spaced electrodes 18. However, other operative elements, such as lumens for chemical ablation, laser arrays, ultrasonic transducers, microwave electrodes, and ohmically heated hot wires, and such devices may be substituted for the electrodes. The spaced electrodes 18 are preferably in the form of wound, spiral coils. The coils are made of electrically conducting material, like copper alloy, platinum, or stainless steel, or compositions such as drawn-filled tubing (e.g. a copper core with a platinum jacket). The electrically conducting material of the coils can be further coated with platinum-iridium or gold to improve its conduction properties and biocompatibility. A preferred coil electrode is disclosed in U.S. Pat. No. 5,797,905. The electrodes 18 are electrically coupled to individual wires 40 (FIG. 7) to conduct coagulating energy to them. The wires are passed in conventional fashion through a lumen extending through the associated catheter body into a PC board in the catheter handle, where they are electrically coupled to a connector that is received in a port on the handle. The connector plugs into a source of RF coagulation energy.

As an alternative, the electrodes may be in the form of solid rings of conductive material, like platinum, or can comprise a conductive material, like platinum-iridium or gold, coated upon the device using conventional coating techniques or an ion beam assisted deposition (IBAD) process. For better adherence, an undercoating of nickel or titanium can be applied. The electrodes can also be in the form of helical ribbons. The electrodes can also be formed with a conductive ink compound that is pad printed onto a non-conductive tubular body. A preferred conductive ink compound is a silver-based flexible adhesive conductive ink (polyurethane binder), however other metal-based adhesive conductive inks such as platinum-based, gold-based, copper-based, etc., may also be used to form electrodes. Such inks are more flexible than epoxy-based inks.

The flexible electrodes 18 are preferably about 4 mm to about 20 mm in length. In the preferred embodiment, the electrodes are 12.5 mm in length with 1 mm to 3 mm spacing, which will result in the creation of continuous lesion patterns in tissue when coagulation energy is applied simultaneously to adjacent electrodes. For rigid electrodes, the length of the each electrode can vary from about 2 mm to about 10 mm. Using multiple rigid electrodes longer than about 10 mm each adversely effects the overall flexibility of the device, while electrodes having lengths of less than about 2 mm do not consistently form the desired continuous lesion patterns.

The portion of the electrodes that are not intended to contact tissue (and be exposed to the blood pool) may be masked through a variety of techniques with a material that is preferably electrically and thermally insulating. This prevents the transmission of coagulation energy directly into the blood pool and directs the energy directly toward and into the tissue. For example, a layer of UV adhesive (or another adhesive) may be painted on preselected portions of the electrodes to insulate the portions of the electrodes not intended to contact tissue. Deposition techniques may also be implemented to position a conductive surface only on those portions of the assembly intended to contact tissue. Alternatively, a coating may be formed by dipping the electrodes in PTFE material.

The electrodes may be operated in a uni-polar mode, in which the soft tissue coagulation energy emitted by the electrodes is returned through an indifferent patch electrode (not shown) externally attached to the skin of the patient. Alternatively, the electrodes may be operated in a bi-polar mode, in which energy emitted by one or more electrodes is returned through other electrodes. The amount of power required to coagulate tissue ranges from 5 to 150 w.

As illustrated for example in FIGS. 6 and 7, a plurality of temperature sensors 42, such as thermocouples or thermistors, may be located on, under, abutting the longitudinal end edges of, or in between, the electrodes 18. Preferably, the temperature sensors 42 are located at the longitudinal edges of the electrodes 18 on the distally facing side of the helical (or other loop) structure. In some embodiments, a reference thermocouple may also be provided. For temperature control purposes, signals from the temperature sensors are transmitted to the source of coagulation energy by way of wires 44 that are also connected to the aforementioned PC board in the catheter handle. Suitable temperature sensors and controllers which control power to electrodes based on a sensed temperature are disclosed in U.S. Pat. Nos. 5,456,682, 5,582,609 and 5,755,715.

The temperature sensors 42 are preferably located within a linear channel 46 that is formed in the distal member 16. The linear channel 46 insures that the temperature sensors will directly face the tissue and be arranged in linear fashion. The illustrated arrangement results in more accurate temperature readings which, in turn, results in better temperature control. As such, the actual tissue temperature will more accurately correspond to the temperature set by the physician on the power control device, thereby providing the physician with better control of the lesion creation process and reducing the likelihood that embolic materials will be formed. Such a channel may be employed in conjunction with any of the electrode (or other operative element) supporting structures disclosed herein.

Finally, the electrodes 18 and temperature sensors 42 can include a porous material coating, which transmits coagulation energy through an electrified ionic medium. For example, as disclosed in U.S. Pat. No. 5,991,650, electrodes and temperature sensors may be coated with regenerated cellulose, hydrogel or plastic having electrically conductive components. With respect to regenerated cellulose, the coating acts as a mechanical barrier between the surgical device components, such as electrodes, preventing ingress of blood cells, infectious agents, such as viruses and bacteria, and large biological molecules such as proteins, while providing electrical contact to the human body. The regenerated cellulose coating also acts as a biocompatible barrier between the device components and the human body, whereby the components can now be made from materials that are somewhat toxic (such as silver or copper).

III. Deployment of Helical Structures

The exemplary catheter 10 may be deployed within a wide variety of body regions. Thus, although the present deployment methods are described by way of example in the pulmonary vein context, they are not so limited.

Referring to FIGS. 8*a–c*, the exemplary catheter 10 may be deployed as follows. First, the sheath 22 may be advanced into the left atrium by a transseptal procedure. The sheath 22 will then be steered directly into the targeted pulmonary vein. Preferably, the sheath 22 will be advanced about 10 to 20 mm into the vein, as illustrated in FIG. 8*a*. If the sheath is not steerable, a steerable catheter (not shown) may be advanced through the sheath and then steered into the targeted pulmonary vein. The sheath will then be advanced over the steerable catheter, just as it would be advanced over a guidewire, to the position illustrated in FIG. 8*a*. The steerable catheter is then withdrawn.

The catheter 10 is then advanced through the sheath 22 with the helical portion in an uncoiled state. The catheter 10 will continue to be advanced until the tip member 26, and about 10 to 20 mm of the anchor member 20, extend beyond the distal end of sheath, i.e. the tip member is about 25 to 35 mm into the vein. [FIG. 8*b*.] Advancing the tip and anchor members to this location allows the helical portion to position itself in the manner described below with reference to FIG. 8*c*. It should be noted that, in some instances, it may be desirable to advance the tip member 26 into one of the branches of the pulmonary vein.

Once the catheter 10 is properly positioned, the helical portion may be deployed. Preferably, this is accomplished by withdrawing the sheath 22 while maintaining the position of the catheter 10 and, more specifically, maintaining the position of the helical portion of the catheter within the pulmonary vein. The helical portion of the catheter 10 will return to its coiled state because it is no longer being constrained by the sheath 22. The tapered helical portion will deploy into the funnel-shaped ostium of the pulmonary vein in such a manner that the atrial tissue will distend and wrap around the helical portion as the helical portion wedges itself into position. Positioning the catheter in the manner illustrated in FIG. 8*b* results in the proximal region of the helical portion (which carries the electrodes 18) being located at the ostium, as is illustrated for example in FIG. 8*c*. The catheter 10 may then, if necessary, be urged in the direction of arrow A to force any helical coils that are proximal of the ostium into contact with the tissue. This positioning of the electrodes 18 insures that tissue coagulation will occur only at the ostium and reduces the likelihood of thermally activated in-vein stenosis.

Diagnostic and/or therapeutic procedures may be performed while the electrodes are, for example, in the position illustrated in FIG. 8*c*. Such procedures include mapping the pulmonary vein and forming a lesion around the pulmonary vein to cure ectopic atrial fibrillation. Finally, after the diagnostic and/or therapeutic procedures have been completed, the catheter 10 may be withdrawn back through the sheath 22.

The above-described steps may, of course, be modified as desired or as variations in catheter structure require. For example, when a catheter such as catheter 37 (FIG. 5) is employed, deploying the helical portion will frequently involve applying a torsional force to the stylet 38, while the returning the helical portion to its uncoiled state will frequently involve applying a torsional force in the opposite direction prior to pulling the catheter back into the sheath. There are also instances where sheaths would not necessarily be required. One such instance involves the use of a catheter having a center support that is activated at a temperature higher than body temperature. Here, the catheter may be advanced into position over guidewire and, when properly positioned, the center support will be heated to return the helical portion to its coiled state. The use of helical catheters without anchor members would require exact positioning within the pulmonary vein so that the helical portion will seat within the ostium without sliding or bouncing out.

Although the present inventions have been described in terms of the preferred embodiments above, numerous modifications and/or additions to the above-described preferred embodiments would be readily apparent to one skilled in the art. It is intended that the scope of the present inventions extend to all such modifications and/or additions and that the scope of the present inventions is limited solely by the claims set forth below.

I claim:

1. A method of treating a pulmonary vein with a helical structure including at least one operative element, the method comprising the steps of:

inserting at least a portion of the helical structure into the pulmonary vein in an uncoiled state;

returning the helical structure to a coiled state while at least a portion of the helical structure is within the pulmonary vein such that the coiled helical structure engages a portion of the pulmonary vein; and performing at least one of a diagnostic and a therapeutic procedure with the at least one operative element.

2. A method as claimed in claim 1, wherein the step of inserting at least a portion of the helical structure into the pulmonary vein comprises:

inserting a tubular member into the pulmonary vein; and passing the helical structure through the tubular member in the uncoiled state.

3. A method as claimed in claim 2, wherein the step of inserting a tubular member into the pulmonary vein comprises inserting a sheath into the pulmonary vein.

4. A method as claimed in claim 2, wherein the step of returning the helical structure to a coiled state comprises pulling the tubular member proximally without substantially moving the helical structure.

5. A method as claimed in claim 1, wherein the step of returning the helical structure to a coiled state comprises moving a tubular member from a position covering the helical structure to a position which does not cover the helical structure.

6. A method as claimed in claim 1, wherein the step of returning the helical structure to a coiled state comprises applying a torsional force to the helical structure.

7. A method as claimed in claim 1, wherein the step of returning the helical structure to a coiled state comprises engaging the pulmonary vein ostium.

8. A method as claimed in claim 1, wherein the step of performing at least one of a diagnostic and a therapeutic procedure comprises forming a lesion.

9. A method as claimed in claim 1, wherein the step of performing at least one of a diagnostic and a therapeutic procedure comprises forming a lesion that extends around the pulmonary vein ostium.

10. A method as claimed in claim 1, wherein the at least one operative element comprises a plurality of electrodes and the step of performing at least one of a diagnostic and a therapeutic procedure comprises transmitting energy with the plurality of electrodes.

11. A method of deploying a helical structure including at least one operative element within a bodily structure defining an orifice, the method comprising the steps of:

inserting at least a portion of the helical structure through the orifice and into the bodily structure in an uncoiled state; and returning the helical structure to a coiled state while at least a portion of the helical structure is within the bodily structure such that the coiled helical structure engages the orifice.

12. A method as claimed in claim 11, wherein the step of inserting at least a portion of the helical structure into the bodily structure comprises:

inserting a tubular member through the orifice into the bodily structure; and passing the helical structure through the tubular member in the uncoiled state.

13. A method as claimed in claim 12, wherein the step of inserting a tubular member through the orifice into the bodily structure comprises inserting a sheath into the bodily structure.

14. A method as claimed in claim 12, wherein the step of returning the helical structure to a coiled state comprises pulling the tubular member proximally without substantially moving the helical structure.

15. A method as claimed in claim 11, wherein the step of returning the helical structure to a coiled state comprises moving a tubular member from a position covering the helical structure to a position which does not cover the helical structure.

16. A method as claimed in claim 11, wherein the step of returning the helical structure to a coiled state comprises applying a torsional force to the helical structure.

17. A method as claimed in claim 11, wherein the step of inserting at least a portion of the helical structure through the orifice and into the bodily structure in an uncoiled state comprises inserting at least a portion of the helical structure through the a pulmonary vein ostium and into the pulmonary vein in an uncoiled state.

* * * * *